United States Patent [19]

Broström

[11] 4,036,875
[45] July 19, 1977

[54] PROCESS FOR THE CONTINUOUS SULPHONATION OF ALKYL AROMATIC HYDROCARBONS

[75] Inventor: Anders Broström, Goteborg, Sweden

[73] Assignee: Berol Kemi AB, Stenungsund, Sweden

[21] Appl. No.: 583,319

[22] Filed: June 2, 1975

[30] Foreign Application Priority Data

June 5, 1974 Sweden .............................. 7407422

[51] Int. Cl.² .......................................... C07C 143/24
[52] U.S. Cl. .......................... 260/505 S; 260/459 R; 260/513 T
[58] Field of Search ..................... 260/505 S, 459 R

[56] References Cited
U.S. PATENT DOCUMENTS

| | | | |
|---|---|---|---|
| 2,768,199 | 10/1956 | Luntz et al. | 260/505 S |
| 3,200,140 | 8/1965 | Sowerby | 260/505 S |

Primary Examiner—Bernard Helfin
Assistant Examiner—A. Siegel

[57] ABSTRACT

An improved process is provided for the continuous sulphonation and/or sulphation of organic substances with sulphur trioxide gas mixed with an inert gaseous diluent, at an increased production rate without impairment of product quality, while minimizing discoloration of the product, and the amounts of unsulphonated product in the product, and of unreacted sulphur trioxide in the residual gaseous mixture, by limiting the amount of sulphur trioxide introduced ab initio into the organic liquid to be sulphonated and/or sulphated to not exceeding 7%, and preferably within the range from about 0.25 to about 5%, of the stoichiometric amount required for the desired sulphonated or sulphated product, introducing the remaining sulphur trioxide over from about 20 to about 80%, preferably from about 25 to about 50%, of the remainder of the length of the reaction zone.

6 Claims, 1 Drawing Figure

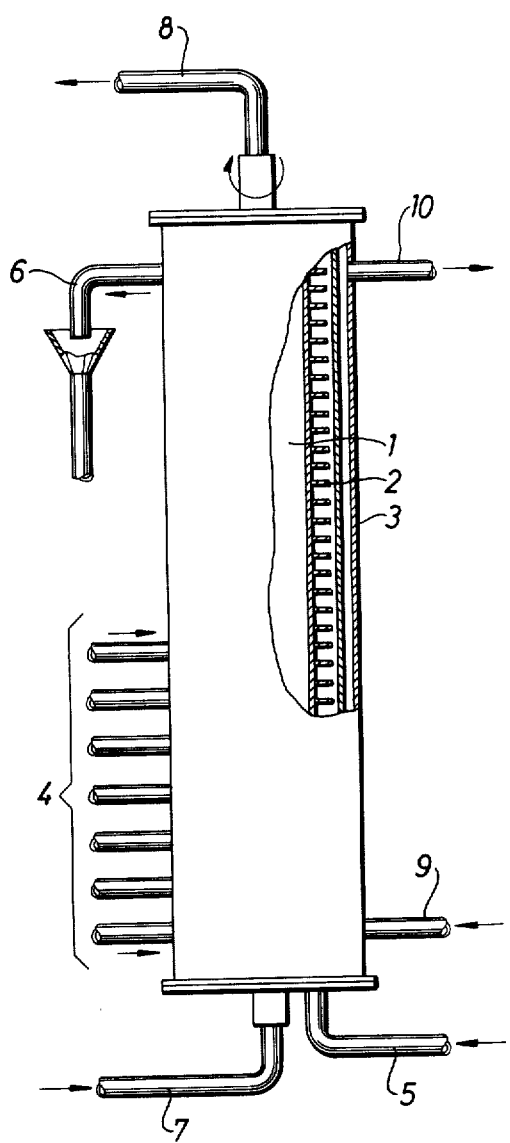

PROCESS FOR THE CONTINUOUS SULPHONATION OF ALKYL AROMATIC HYDROCARBONS

Sulphonation and/or sulphation processes involving the use of sulphur trioxide are highly exothermic, and to prevent discoloration of the finished product by the decomposition products, the sulphur trioxide gas should be diluted with a large amount of inert gas, such as air, carbon dioxide, nitrogen or sulphur dioxide gas, with coolant to remove the heat of the reaction from the reaction zone as quickly as possible. When carrying out the process in batches it is relatively simple, in the initial stages, to maintain favorable reaction conditions, since it is then possible to work with a large volume of unreacted organic substance in proportion to sulphur trioxide, and the exothermic heat of the reaction can be taken up by cooled surfaces of the apparatus upon rapid stirring in the reaction mixture. However, as the degree of sulphonation and/or sulphation increases, the viscosity of the reaction mixture also increases, interfering with and slowing heat transfer, resulting in local overheating and discoloration of the product. The rise in viscosity increases the mechanical energy applied, and the reaction time. Normally, a batchwise reaction of 1000 kg of raw material takes about four hours.

In order to reduce the reaction time and improve heat distribution, continuous reaction methods have been proposed, which, provided certain reaction conditions are satisfied, permit a very short reaction time, for example, less than one minute. In order to ensure a good result, however, it is then necessary that the sulphur trioxide gas be diluted with a large amount of an inert gas, so that the concentration of sulphur trioxide in the gas mixture is preferably below about 7%. This means that, for example, in the sulphonation of dodecyl benzene, it is necessary to react about 1000 liters of gas per liter of raw material. In such a continuous sulphonation and/or sulphation process, it is extremely important for the organic substance to be mixed with the gaseous mixture containing sulphur trioxide gas as quickly as possible. The organic raw material should preferably be present in the liquid phase, and during reaction, the gaseous sulphur trioxide reaction mixture should be present in this liquid in a dispersed form. Further, the heat of reaction should be removed as quickly as possible, so that the reaction temperature nowhere exceeds 80° C, and is preferably within the range from about 20° to about 70° C, as otherwise the product will be dark in color. It is also extremely important to remove the reaction product from the reaction zone as quickly as possible.

According to U.S. Pat. Nos. 3,438,742 and 3,438,743 to Grunewald et al and U.S. Pat. No. 3,438,744 to Steijner, issued Apr. 15, 1969, the continuous sulphonation and/or sulphation is carried out by introducing organic substances and sulphur trioxide mixed with an inert gaseous medium through one or more separate inlets (Example 5 of U.S. Pat. No. 3,438,742 uses three inlets) in one end of a reactor, consisting essentially of at least one fixed stator, and a concentric rotor defining an annular reaction chamber therebetween, with some sort of mixing device, whose function is to intimately mix the two reactants in that chamber, so that a rapid and effective sulphonation or sulphation is obtained. The reaction mixture is introduced at one end of the reactor and rapidly passed through the reactor, in the course of which sulphur trioxide and the organic substance react, and the reaction product is taken out at the other end. If desired, the reactor can be divided into several separate reaction zones, by connecting several stators in series, or by providing a stator with partition walls.

According to one embodiment, the mixing device includes a plurality of projections or pips on the surface of the cooled stator, or the rotor, or both. If the annular reaction zone is sufficiently narrow a very good cooling and a very short product dwell time are possible. A good dispersion of the sulphonating or sulphating gas mixture in the organic liquid is obtained, due to the turbulent movement of the reaction mixture, and local oversulphonation accompanied by discoloration is avoided without stopping the movement of the reaction products towards the outlets.

In either batch or continuous sulphonation or sulphation processes, the entire amount of sulphur trioxide required can be mixed with the organic liquid at the start of the reaction. However, in such cases, a far too rapid reaction can be initiated, which results in discoloration of the product. Therefore, as in Example 5 of U.S. Pat. No. 3,438,742, the feed of sulphur trioxide can be distributed among three inlets along the lower third of the reactor. At least 10%, preferably at least 15%, of the stoichiometric amount of sulphur trioxide is introduced through the first inlet for sulphur trioxide, since by introducing relatively large amounts of sulphur trioxide in the initial stages of the reaction, the potential capacity of the reactor can be utilized effectively, achieving a relatively low proportion of unsulphonated product and unreacted sulphur trioxide in the residual gaseous mixture, and a high production speed, while reducing the risk of discoloration.

According to the present invention it has been found that in the continuous sulphonation and/or sulphation of organic liquids in an elongated reaction zone, the production rate can be considerably increased, while minimizing discoloration of the product, and the amounts of unsulphonated product in the product, and of unreacted sulphur trioxide in the residual gaseous mixture, if the amount of sulphur trioxide introduced ab initio into the organic liquid to be sulphonated and/or sulphated does not exceed 7%, and preferably is within the range from about 0.25 to about 5%, of the stoichiometric amount required for the desired sulphonated or sulphated product. The point of introduction of such sulphur trioxide is considered the start of the reaction zone, and the point of withdrawal of the reaction product is considered the end of the reaction zone. The introduction of the remaining sulphur trioxide should be distributed over from about 20 to about 80%, preferably from about 25 to about 50%, of the remainder of the length of the reaction zone, measured from the start of the reaction zone. If sulphur trioxide is added in the last 20% of the reaction zone, much of this sulphur trioxide will not react with the organic substance, but is removed in the residual gas. In the first 15% of the reaction zone, measured from the start, the amount of sulphur trioxide preferably does not exceed 25% of the stoichiometric amount.

The reason why an extremely low proportion of sulphur trioxide in the initial stages of the sulphonation and/or sulphation reaction results in a higher production rate and a higher total production is not understood.

A possible explanation is that the organic substance is extremely sensitive to sulphonation or sulphation, but as the amount of sulphonation or sulphation product increases, this sensitivity is reduced, so that the total amount of sulphonated or sulphated products, while maintaining good product quality can be increased by about 40%, compared to the best conventional methods now available.

The sulphonation is carried out at a temperature within the range from about 15° C to about 100° C, preferably from about 20° C to about 80° C.

The process can be used for the sulphonation and/or sulphation of any organic substance, such as aliphatic and cyclic (carbocyclic and heterocyclic) compounds, preferably in the liquid phase. Solid materials can be liquefied, or dissolved or dispersed in an inert liquid. Examples of such compounds are fatty alcohols, which preferably hve a $C_8 - C_{22}$ carbon chain; ethylene oxide adducts of fatty alcohols and fatty acids; alkyl aryl compounds such as keryl benzene, nonyl benzene, dodecyl benzene, nonyl phenol, nonyl naphthalene, and olefins having from eight to twenty four carbon atoms. Naturally, the raw material may also contain mixtures of such compounds. It is also possible to add to the organic liquid substrate inert additives which themselves will not be sulphonated and/or sulphated, to act as, for example, viscosity reducers or solvents. Examples of such additives are ethylene dichloride and acetic acid. These substrates can be added prior to, during, or after the sulphonation process, depending on the purpose the additive is to serve.

When using sulphur trioxide as sulphonating and/or sulphating agent, a highly accurately determined amount of sulphur trioxide must be charged to a definite amount of substance to be sulphonated, and the sulphur trioxide in gaseous state is mixed with air, nitrogen or other inert gas. In such mixtures, the amount of sulphur trioxide normally does not exceed 15% and is preferably less than 7%.

Sulphonation with sulphur trioxide usually is carried out with 2 to 8 mole percent in excess of the theoretically required amount of sulphur trioxide. This is called a sulphonation degree of 102 to 108%. The amount of added sulphur trioxide is critical. Too low a sulphonating degree results in a greater or smaller amount of unsulphonated raw material in the production and may bring about undesirable side effects, for example turbidity, when the product is being applied. Too high a sulphonating degree gives rise to a substantial discoloration of the product, caused by side reactions in the form of, for example, decomposition of the organic substance. As a result thereof, there will be raw material losses as well as a discolored final product which is hard to bleach. Especially in such cases when alkylene oxide derivatives of fatty alcohols and alkyl phenols are sulphonated with sulphur trioxide, the product obtained shows foaming properties of a troublesome nature.

The process of the invention can be carried out in any of the types of apparatus for carrying out the continuous sulphonation and/or sulphation process described in U.S. Pat. Nos. 3,438,742, 3,438,743 and 3,438,744. The apparatus shown in U.S. Pat. No. 3,438,742 illustrates three suitable types of protruding members, viz. cylindrical pegs (2, FIG. 2), conical pegs (21, FIG. 3) and flat, profilated, throughgoing members (22, FIG. 4), showing their arrangement on the movable cooling surface.

The protruding members can be designed in many different ways, but an indispensable condition is that they are so designed and positioned on the movable cooling surface that no so-called dead zones appear in their vicinity, where reacted product can remain in the form of lumps with a higher viscosity and thereby be oversulphonated or oversulphated, resulting in discoloration of and uneven degree of sulphonation or sulphation in the final product. This is of particular importance in the sulphonation and/or sulphation of highly viscous, organic liquids. The protruding members must thus not put up any great resistance to the flow of the reaction mixture towards the outlet. They can, for instance, be made in the form of largely cylindrical or conical pegs or pins with a largely circular cross-section, which are affixed to the movable cooling surface at an appropriate distance from one another. The height of the pegs will naturally depend on the distance between the two cooling surfaces and on the speed of the moving cooling surface in relation to the stationary cooling surface. The height should be as great as the available space between the cooling surfaces, with due regard to what is permitted by the manufacturing tolerance. In this way, the formation of poor heat-conducting layers between the stationary cooling surface and the liquid/gas dispersion is avoided and the liquid turnover is increased. A suitable dimension for the height of said pegs has been found to be 0.5 to 0.9 times the distance between the two cooling surfaces at a relative speed of 5 to 15 meters per second on the part of the moving cooling surface, but in certain cases the height can be even smaller, e.g., down to 0.1 times the said distance. If the pegs are largely cylindrical in shape as shown at 2 in FIG. 2, they should have a cross-sectional dimension of 0.1 to 1 times the distance between the two cooling surfaces. If conical pegs are used as shown in 21 in FIG. 3, the base of the cone can be located on the moving cooling surface. The tip of the cone should be cut off squarely and should not display a diameter smaller than that for cylindrical pegs. It is also possible with regard to conical pegs to allow the base of the cone to be turned towards the stationary cooling surface in order to improve the retention of the organic liquid on the rotating cooling surface, although this form of design involves higher manufacturing costs in respect of the apparatus. The distance between the pegs is dependent on the relative speed of the moving cooling surface and should be chosen so that as intensive dispersion of the organic liquid as possible is obtained. The pegs, however, must not be too close to one another, as in such cases gas-filled strings may develop between the pegs, without sufficient liquid turnover in the surface layer of the strings, thereby creating a risk of oversulphonation and/or oversulphation and the resultant product will be discolored. A suitable distance between the pegs has been found to be about 8 to 20 peg diameters, measured in the direction of motion of the moving cooling surface at the above-mentioned relative speed. This distance is preferably 9 to 15 peg diameters and a distance of about 10 peg diameters has proved particularly suitable. At right angles to the direction of motion of the moving cooling surface, the best result is obtained with a distance of about 3 peg diameters or more. Good results have been obtained with a distance in this direction of 4 to 15 peg diameters, a distance of about 5 peg diameters having proved particularly suitable.

The protruding members may also be in the form of baffles, i.e., largely rectangular or square, flat members, as shown at 22 in FIG. 4, applied along the whole or a part of the moving cooling surface, which may possibly be provided with drilled recesses to achieve an intensified contact. If such flat protruding members are utilized, these should preferably not be throughgoing and alike over the entire cooling surface, but in order to reduce the tendency to form gas bubbles behind the baffle should be patterned in the form of cut-off parts 23, as shown in FIG. 4. The most protruding parts of the protruding members can be displaced in relation to one another so as to form a coil in the direction of flow. A suitable design of baffle has been found to have a largely rectangular cross-section in the direction of motion with a height of 0.2 to 0.9 times the distance between the cooling surfaces and a width of 2 to 15 times the distance between the cooling surfaces, and with rectangular recesses as shown in FIG. 4 with a height of 0.3 to 0.7 and a width of 3 to 4 times the distance between the cooling surfaces. Suitable distances between the baffles in the direction of motion of the moving cooling surface are between 1 and 10 times the distance between the cooling surfaces.

To allow regulation of the time during which the product remains in the reaction apparatus, the protruding members can be arranged in the form of a spiral along the moving cooling surface, if the latter is made in the form of a circular rotor as shown in FIGS. 2 to 4. It is thereby made possible to adapt in a suitable manner the amount of organic liquid in relation to the amount of $SO_3$ contained in the gas mixture. If, for example, the protruding members are arranged in a spiral which endeavors to press the reaction mixture towards the outlet opening, the time during which the organic liquid remains in the reactor is cut down, whereas the opposite result is obtained if the spiral is turned in the other direction. In order to ensure the best possible dispersion, pegs or baffles should be so displaced in relation so succeeding or following pegs or baffles in the direction of flow that every portion of the stationary cooling surface will be passed by the tip of a peg or baffle at a very short distance during one cycle.

Another embodiment of the protruding members can be in the form of a perforated steel mat, placed on top of and affixed to the moving cooling surface. The preferred embodiment of the protruding members, however, is substantially cylindrical pegs.

The relative speed of the moving cooling surface should be kept as high as possible in order to attain the best dispersing effect and so that the coefficient of heat transfer will be as favorable as possible. The speed, however, must not be so high that the organic liquid is thrown away from the moving cooling surface and over onto the stationary cooling surface, forming a layer on the latter so that the gas mixture has to pass in a liquid-less space between the two cooling surfaces. This would result in both poor dispersion of the gas mixture in the organic liquid and a poor coefficient of heat transfer on the moving cooling surface. Both of these factors give rise to discoloration of the final product. If the moving cooling surface is designed as a largely cylindrical rotor arranged concentrically within a largely cylindrical, outer, stationary cooling surface, a speed of 300 to 1500 r.p.m., preferably 500 to 700 r.p.m., has proved suitable. A speed of about 600 r.p.m. has been found particularly suitable.

The mixture of sulphur trioxide gas and inert gas should, in order to avoid any reaction outside the reaction apparatus, be introduced into this annular reaction space at a plurality of points separated from the supply point for the organic substance, e.g., at seven separate points in one end of the reaction apparatus, as shown in FIG. 1 hereof. It is also possible to introduce the organic substance through the end of the reaction apparatus and to introduce the sulphonating gas through nozzles affixed to the sides of the reaction apparatus. The apparatus shown in the drawings is purely schematic and includes only such parts as are essential in order to impart an understanding of the idea of the invention. Other details which may be required in order to impart mechanical perfection to the arrangement but which have no bearing on the actual idea of the invention and can easily be designed by the technicians have been excluded. These include, for instance, the detailed shaping of bearings, gaskets for shaft passages, cooling devices, etc. The parts shown can also be modified in numerous ways within the framework formed by the idea of the invention. The arrangement, for instance, can work with a vertical or horizontal axis of symmetry or in any and every intermediate position and the protruding members can have other cross-sections than largely circular ones, when pegs are used, for example elliptical.

The arrangement as shown in FIG. 1 is characterized by a largely cylindrical drum 1, rotatable around its axis of symmetry and cooled on the inside, which is provided on the whole or major part of its outside with a number of projecting pegs 2 to cause turbulence in the medium surrounding the members upon rotation of the drum, by a stationary, outer cooling jacket 3 which surrounds the drum concentrically; seven inlets 4 and inlet 5 for the sulphur trioxide gas mixture and the organic substance, respectively; outlet 6 for reaction product and residual gas mixture; inlet 7 and outlet 8 for cooling of the rotating drum; and inlet 9 and outlet 10 for cooling of the cooling jacket 3 surrounding the drum.

The method according to the invention can be suitably carried out in such an apparatus. The process of the invention is not limited to the use of this apparatus, but can be carried out in any apparatus for sulphonation or sulphation of organic substances with gaseous sulphur trioxide.

Preferred embodiments of the invention are given in the following Examples:

EXAMPLES 1 AND 2

A reactor constructed as illustrated in FIG. 1 was used for the sulphonation of dodecyl benzene. The reactor consisted of a stator 3, provided with a cooling jacket, having a cooled water inlet 9 and outlet 10. A rotor 1, driven around by a motor, was placed inside the stator. The interior of the rotor was cooled by means of the water inlet 7 and outlet 8. Affixed round the rotor were pegs 2, having a diameter of 1 mm and a length of 7 mm. The inside diameter of the stator was 520 mm and the outside diameter of the rotor was 494 mm. The pegs were placed 10 mm from one another in the form of a spiral, rising 10 mm per turn. The length of the rotor was 2465 mm and that of the stator 2490 mm. Sulphur trioxide gas was introduced through twenty nozzles 4, divided into two sets of ten nozzles each, placed on each side of the reactor, and spaced 80 mm apart along the reactor. The organic substance was introduced through the bottom inlet 5, and the product and residual gas mixture were removed via outlet 6, at the top of the reactor, for separation.

At the same time as a mixture of sulphur trioxide and air containing 6% $SO_3$ was introduced through the nozzles 4 in the distribution shown in Table I below, dodecyl benzene was introduced through bottom inlet 5 in the molar ratio moles $SO_3$:moles dodecyl benzene of 1.04 :1. By increasing the feed rate of the mixture of sulphur trioxide and air and of dodecyl benzene gradually, the highest production rate was determined, while maintaining a sulphonation degree, calculated as converted $SO_3$, of at least 99%, unsulphonated dodecyl benzene not exceeding 2%, and a color quality not exceeding 250 Hazen in a 15% ethanol solution.

In this way, four runs were made at the different distribution ratios among the twenty nozzles arranged in ten rows of two nozzles each, shown in the Table.

TABLE I

| | $SO_3$ distribution in % $SO_3$ of the total gas | | | |
|---|---|---|---|---|
| | | | EXAMPLE NO. | |
| Row No.[1] | Control 1 | Control 2 | 1 | 2 |
| 1 | 10 | 16.7 | 3.3 | 4.0 |
| 2 | 10 | 16.7 | 3.3 | 3.0 |
| 3 | 10 | 13.3 | 6.7 | 3.0 |
| 4 | 10 | 13.3 | 6.7 | 3.7 |
| 5 | 10 | 10.0 | 10.0 | 11.9 |
| 6 | 10 | 10.0 | 10.0 | 11.9 |
| 7 | 10 | 0.7 | 13.3 | 3.7 |
| 8 | 10 | 0.7 | 13.3 | 3.7 |
| 9 | 10 | 3.3 | 16.7 | 6.0 |
| 10 | 10 | 3.3 | 16.7 | 49.1 |
| RESULTS: | | | | |
| Production rate (kilos dodecyl benzene sulphonic acid/hour) | 475 | 364 | 557 | 600 |
| Color in a 15% ethanol solution (Hazen) | 250 | 250 | 250 | 250 |
| % Conversion of $So_3$ | 99 | 100 | 99 | 99 |
| % Unsulphonated organic material | 1.6 | 1.4 | 1.6 | 1.6 |

[1]Two nozzles in each row, on opposite sides of the reactor

The Examples show that a much higher production rate is obtained by reducing the amount of added gaseous $SO_3$ to below 7% in Nozzle No. 1.

EXAMPLE 3

The same reactor as in Examples 1 and 2 was used to sulphonate technical lauryl alcohol. The introduced gaseous air-sulphur trioxide mixture contained 3% by volume $SO_3$, and was distributed via the sets of nozzles according to Table II in a molar ratio $SO_3$: lauryl alcohol of 1:1. The highest possible production rate while maintaining good product quality was determined in the same way as in Examples 1 and 2.

TABLE II

| | $SO_3$ distribution in % $SO_3$ of total gas | |
|---|---|---|
| Row No.[1] | Control | Example No. 3 |
| 1 | 10 | 4.0 |
| 2 | 10 | 3.0 |
| 3 | 10 | 3.0 |
| 4 | 10 | 3.7 |
| 5 | 10 | 11.9 |
| 6 | 10 | 11.9 |
| 7 | 10 | 3.7 |
| 8 | 10 | 3.7 |
| 9 | 10 | 3.7 |
| 10 | 10 | 49.1 |
| RESULTS: | | |
| Production rate (kilos dodecyl benzene sulphonic acid/hour) | 300 | 370 |
| Color in a 15% ethanol solution (Hazen) | 75 | 75 |
| % Conversion of $SO_3$ | 99 | 99 |
| % Unsulphonated organic material | 2.1 | 2.3 |

[1]Two nozzles in each row, on opposite sides of the reactor

By limiting the sulphur trioxide gas to less than 7% in Nozzle No. 1, the capacity of the reactor can be increased by almost 25%.

Having regard to the foregoing disclosure, the following is claimed as the inventive and patentable embodiments thereof:

1. In the process for the continuous sulphonation of an alkyl aromatic hydrocarbon in the liquid phase with sulphur trioxide gas in an elongated reaction zone, the point of introduction of such sulphur trioxide gas being the start of the reaction zone, and the point of withdrawal of the reaction product being the end of the reaction zone, the improvement which comprises limiting the amount of sulphur trioxide introduced initially at the start of the reaction zone into the liquid phase to be sulphonated to not exceeding 7% of the stoichiometric amount required for the desired sulphonated product, and distributing the introduction of the remaining stoichiometric amount of sulphur trioxide gas over from about 20 to about 80% of the remainder of the length of the reaction zone.

2. A process according to claim 1, in which the amount of sulphur trioxide introduced initially into the liquid phase is within the range from about 0.25 to about 5%, and distributing the introduction of the remaining stoichiometric amount of sulphur trioxide gas over from about 25 to about 50% of the remainder of the length of the reaction zone.

3. A process according to claim 1, in which in the first 15% of the reaction zone, measured from the start, the amount of sulphur trioxide introduced does not exceed 25% of the stoichiometric amount.

4. A process according to claim 1, in which the sulphonation is carried out at a temperature within the range from about 15° C to about 100° C.

5. A process according to claim 1, in which the sulphonation is carried out at a temperature within the range from about 20° C to about 80° C.

6. A process according to claim 1, in which the sulphur trioxide is introduced in admixture with an inert gas.

* * * * *